US 11,971,547 B2

United States Patent
Profendiner

(10) Patent No.: US 11,971,547 B2
(45) Date of Patent: Apr. 30, 2024

(54) CONTROL APPARATUS AND METHOD FOR REDUCING MOTION SICKNESS IN A USER WHEN LOOKING AT A MEDIA CONTENT BY MEANS OF SMART GLASSES WHILE TRAVELLING IN A MOTOR VEHICLE

(71) Applicant: AUDI AG, Ingolstadt (DE)

(72) Inventor: Daniel Profendiner, Ingolstadt (DE)

(73) Assignee: AUDI AG, Ingolstadt (DE)

( * ) Notice: Subject to any disclaimer, the term of this patent is extended or adjusted under 35 U.S.C. 154(b) by 0 days.

(21) Appl. No.: 17/266,895

(22) PCT Filed: May 21, 2019

(86) PCT No.: PCT/EP2019/063020
§ 371 (c)(1),
(2) Date: Feb. 8, 2021

(87) PCT Pub. No.: WO2020/035185
PCT Pub. Date: Feb. 20, 2020

(65) Prior Publication Data
US 2021/0318539 A1    Oct. 14, 2021

(30) Foreign Application Priority Data
Aug. 13, 2018    (DE) .................... 10 2018 213 588.6

(51) Int. Cl.
*G02B 27/01* (2006.01)
*A61M 21/00* (2006.01)
*G02B 27/00* (2006.01)

(52) U.S. Cl.
CPC .......... *G02B 27/017* (2013.01); *A61M 21/00* (2013.01); *G02B 27/0093* (2013.01);
(Continued)

(58) Field of Classification Search
CPC ................. G06F 3/011; G06F 3/04815; G02B 2027/014; G02B 2027/0183;
(Continued)

(56) References Cited

U.S. PATENT DOCUMENTS

| 9,283,349 | B2 | 3/2016 | Yeh | |
| 2014/0176296 | A1* | 6/2014 | Morgan | G06F 3/011 340/4.13 |

(Continued)

FOREIGN PATENT DOCUMENTS

| DE | 101 56 219 C1 | 8/2003 |
| DE | 10 2014 019 579 A1 | 6/2016 |

(Continued)

OTHER PUBLICATIONS

International Preliminary Report on Patentability (Forms PCT/IPEA/409; PCT/IPEA/416); dated Oct. 16, 2020, in International Patent Application No. PCT/EP2019/063020, including Transmittal Letter and Amended Claims (25 pages).

(Continued)

*Primary Examiner* — Ram A Mistry
(74) *Attorney, Agent, or Firm* — STAAS & HALSEY LLP

(57) ABSTRACT

Motion sickness of a user occurring when viewing media content by use of data glasses during a journey in a motor vehicle is reduced. Vehicle dynamics data and glasses dynamics data are registered and a displayed perspective is controlled by a control device based on the vehicle dynamics data and the glasses dynamics data. In the displayed perspective, the media content is displayed in a media field which is shown so it is visible through a frame element and an artificial environment is shown adjacent to the frame element. A velocity component of the vehicle dynamics data is represented as movement of the artificial environment and (Continued)

an acceleration component of the vehicle dynamics data is represented by an inclination of the frame element with respect to the media field and a movement component of the glasses dynamics data is represented as a shift of the entire perspective.

18 Claims, 2 Drawing Sheets

(52) U.S. Cl.
CPC ........... *A61M 2021/0005* (2013.01); *G02B 2027/014* (2013.01); *G02B 2027/0183* (2013.01); *G02B 2027/0187* (2013.01)

(58) Field of Classification Search
CPC ........ G02B 2027/0187; G02B 27/0093; G02B 27/017; A61M 2021/0005; A61M 21/00
See application file for complete search history.

(56) References Cited

U.S. PATENT DOCUMENTS

| | | | | |
|---|---|---|---|---|
| 2015/0097863 | A1* | 4/2015 | Alaniz | G06F 3/011 |
| | | | | 345/633 |
| 2016/0048027 | A1 | 2/2016 | Shpigelman | |
| 2018/0081426 | A1 | 3/2018 | Rothkopf | |
| 2018/0089901 | A1* | 3/2018 | Rober | B60Q 9/00 |

FOREIGN PATENT DOCUMENTS

| | | |
|---|---|---|
| DE | 10 2015 003 882 A1 | 9/2016 |
| WO | 2018/057980 A1 | 3/2018 |

OTHER PUBLICATIONS

Notification of Transmittal of Translation of the International Preliminary Report on Patentability (Form PCT/IB/338); dated Feb. 18, 2021, in International Patent Application No. PCT/EP2019/063020 (1 page).
International Search Report (Forms PCT/ISA/210; PCT/ISA/220; and PCT/ISA/237); dated Jul. 31, 2019, in International Patent Application No. PCT/EP2019/063020 (19 pages).
Written Opinion (Form PCT/IPEA/408); dated Apr. 21, 2020, in International Patent Application No. PCT/EP2019/063020 (8 pages).
Examination Report dated Jun. 17, 2019, in German Patent Application No. 10 2018 213 588.6 (12 page). X
International Preliminary Report on Patentability (Forms PCT/IPEA/409; PCT/IPEA/416); dated Oct. 16, 2020, in International Patent Application No. PCT/EP2019/063020, including Transmittal Letter and Amended Claims (18 pages).
Phillip Hock et al.; "CarVR: Enabling In-Car Virtual Reality Entertainment"; Experiences with Virtual Reality, CHI 2017, May 6-11, 2017, pp. 4034-4044.
International Patent Application No. PCT/EP/2019/063020, May 21, 2019, Daniel Profendiner, AUDI AG.
German Patent Application No. 10 2018 213 588.6, Aug. 13, 2018, Daniel Profendiner, AUDI AG.

* cited by examiner

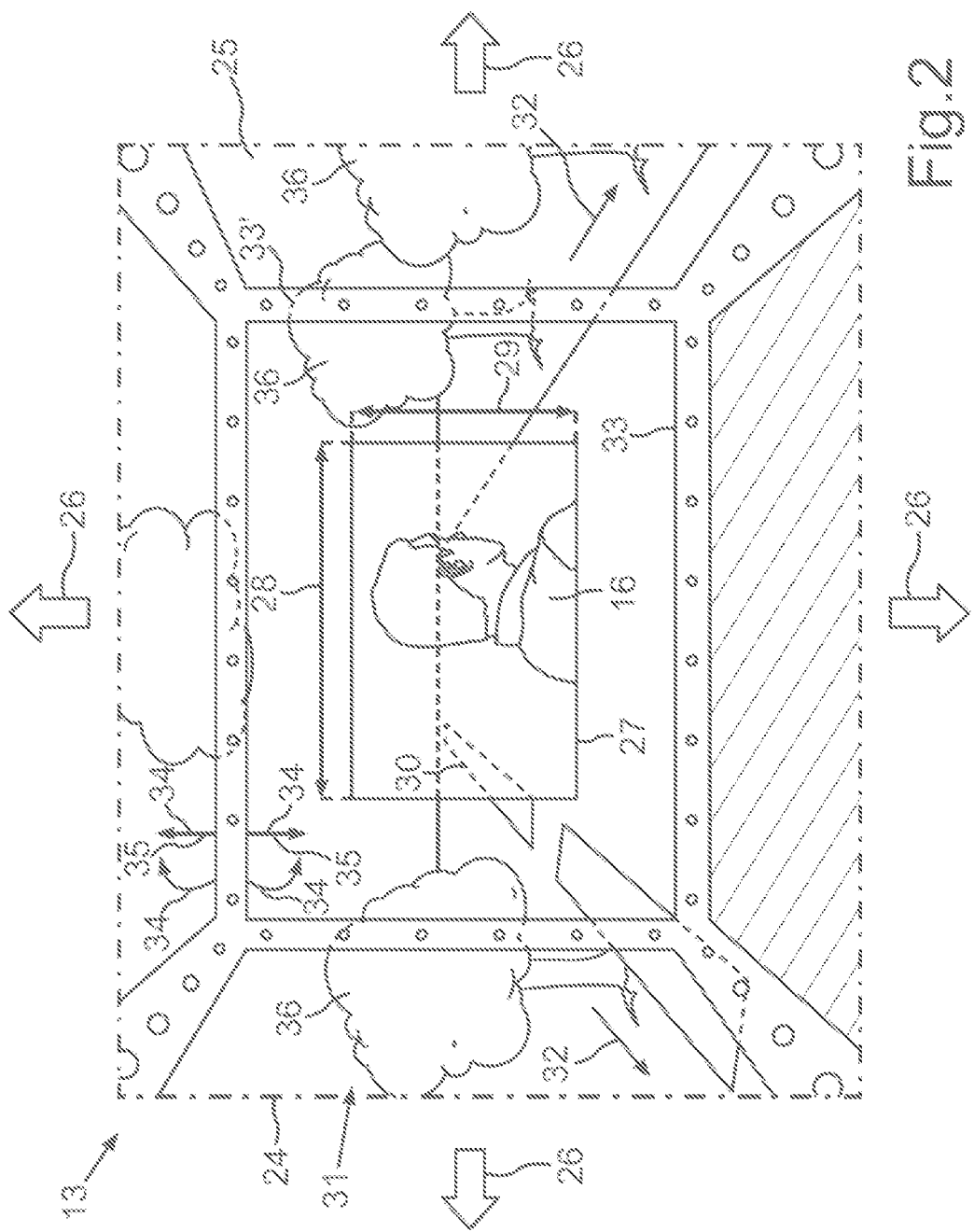

CONTROL APPARATUS AND METHOD FOR REDUCING MOTION SICKNESS IN A USER WHEN LOOKING AT A MEDIA CONTENT BY MEANS OF SMART GLASSES WHILE TRAVELLING IN A MOTOR VEHICLE

CROSS-REFERENCE TO RELATED APPLICATIONS

This application is a U.S. national stage of International Application No. PCT/EP2019/063020, filed on May 21, 2019. The International Application claims the priority benefit of German Application No. 10 2018 213 588.6 filed on Aug. 13, 2018. Both the International Application and the German Application are incorporated by reference herein in their entirety.

BACKGROUND

Described herein is a method for reducing motion sickness (kinetosis) which a user can feel when viewing media content (for example an entertainment film) when he uses data glasses (smart glasses) for the viewing during a journey with a motor vehicle. Also described herein is a control device for data glasses of a motor vehicle. Also described herein is a motor vehicle having such a control device.

In a system for using so-called virtual reality (VR) in a motor vehicle, work is being done so that in addition to fully immersive games, 2D media content (films, text, presentations, to mention only examples) can be used without feeling motion sickness or with a reduced feeling of motion sickness. The virtual reality is conveyed in this case by use of data glasses, which close off the eyes of the user in a light-tight manner toward the surroundings and instead a virtual space is displayed from an artificial perspective, i.e. from an artificial observation point, for each eye in the field of view of the user by use of a respective display screen. The display content of the virtual reality (i.e., the virtual space) displayed from the perspective is adapted here with respect to a movement of a head of the user, whereby the user feels a so-called immersive experience, i.e., a correlation between a movement of his head and the perspective changing with it. A movement-correlated perspective thus results for the user, as would also result without data glasses during the observation of the real environment.

However, additional movements of the motor vehicle itself result during the use in a motor vehicle (translational movement during driving and rotation, for example, during cornering or during pitching), which does not necessarily have to be depicted in the display content of the virtual reality if the user keeps the head still with respect to the motor vehicle during this. The user then feels an acceleration force of the vehicle movement for which there is no visual correspondence in the virtual reality. This results in the motion sickness.

German Patent Application No. 10 2014 019 579 A1 describes that the media content to be displayed can be shown in a partially transparent manner by use of the data glasses and an artificial background or an artificial environment can also be shown together with the media content by use of the partially transparent display, the objects of which move in accordance with the motor vehicle movements in relation to the perspective displayed in the data glasses (i.e., the virtual standpoint of the user and his virtual viewing direction). This does reduce the motion sickness, but results in movement fragments of the partially transparently displayed background in the media content shown or displayed.

Displaying the media content only in a media field reduced in size, i.e., a predetermined image region, by use of the data glasses, and tilting this media field as a function of signals of a movement and position sensor of the vehicle in order to visually convey the movement of the motor vehicle with respect to the environment to the user of the data glasses in this way is described in German Patent Application Publication No. 101 56 219 C1. However, this has the result that the media content tilts back and forth from the perspective of the user.

Reducing the motion sickness in that an artificial, resting horizon is overlaid and in addition artificial environmental objects are animated in a peripheral region of the view of the user, which move past the virtual viewpoint of the user according to the movement of the motor vehicle, is described in International Application Publication No. 2018/057980 A1. In this way, however, an acceleration and a deceleration of the motor vehicle cannot be directly conveyed visually, but rather a faster or slower drift speed of the virtual objects only results indirectly. However, visually conveying acceleration forces is what is crucial here.

Therefore, the main influence for motion sickness, namely the effect of the acceleration forces on the sense of equilibrium of the user, cannot be conveyed in a visually corresponding manner using the solutions described in the related art.

SUMMARY

One or more aspects of the disclosure include reducing the motion sickness of the user when viewing media content in the case of the use of data glasses during a journey of a motor vehicle.

This may be achieved by the method for reducing motion sickness, control device for data glasses of a motor vehicle, and the motor vehicle having the control device, described herein. Advantageous embodiments are also described herein, with reference to the following description, and the drawings.

The disclosure provides a method for reducing motion sickness of a user when viewing media content. The method presumes that the user views the media content by use of data glasses during a journey in a motor vehicle. Vehicle dynamics data, which describe a movement of the motor vehicle with respect to its real environment, and glasses dynamics data, which describe a movement of the data glasses with respect to the motor vehicle and/or the real environment, are registered in a way known per se. A perspective which is displayed to the user by use of the data glasses is controlled by a control device as a function of the vehicle dynamics data and the glasses dynamics data. The perspective is a virtual viewpoint or virtual position and also a virtual viewing direction of the display content of the data glasses, i.e., for example on or in a virtual space. It is thus a perspective in a virtual reality or a virtual space.

During the journey in the motor vehicle, while an action of a (translational and/or rotational) acceleration force occurs on the user due to the movement of the motor vehicle, in order to depict or visually represent this in the displayed perspective, it is provided according to the disclosure that the media content be displayed in a media field in the displayed perspective, i.e., for example, a virtual movie screen or a rectangular field. In the described way, for example, a video film or a text or a data presentation can be provided as the media content, to only mention examples. The media field is displayed visibly through a frame element in this case (observed from the displayed perspective), wherein the frame element at least partially, for example completely encloses the media field. Such a frame element can thus be, for example, a picture frame or can be displayed as a window frame of a virtual cockpit. The frame element is part of the graphic display and thus includes, for example, at least one pixel-based graphic object. An artificial environment is displayed adjacent to the frame element and/or through a partially-transparent region of the frame element. The artificial environment represents the real environment with respect to a relative movement in this case. The artificial environment is also part of the graphic display, and thus includes at least one pixel-based graphic object.

A velocity component of the vehicle dynamics data, i.e., a specification of the travel velocity of the motor vehicle with respect to the real environment, is now shown as a movement of the artificial environment with respect to the frame element. In other words, the artificial environment moves past the frame element like the real environment moves past the motor vehicle. An acceleration component of the vehicle dynamics data, i.e., acceleration data relating to a velocity change and/or direction change of the vehicle in the real environment, is represented by an inclination or displacement of the frame element with respect to the media field. An acceleration component is thus represented visually in the displayed perspective in that the frame field changes with respect to the media field in regard to the relative position. In contrast, a movement component of the glasses dynamics data, i.e., movement data which describe a movement of the head of the user in relation to the motor vehicle and/or the real environment, is or shown as a shift of the entire perspective. The user thus still has the impression in this way that he can move freely in a space with respect to all displayed elements. The media field can also stop unmoved or can be turned with the head. In the latter case, the media content thus remains in the field of view of the user even if he turns his head to the side.

An evaluation with test subjects has had the result that this method provides the advantage that users can now visually associate acceleration forces which they perceive during the journey of the motor vehicle due to their sense of equilibrium in that the frame element inclines with respect to the media field and also with respect to the moving artificial environment. In the tests, this has resulted in an advantageous reduction of the motion sickness.

However, not simply only the velocity component and the acceleration component of the vehicle data are visually represented by the method for this purpose, but rather due to the described use of the velocity component for the representation of the movement of the artificial environment and the use of the acceleration component for the representation of the inclination or shift of the frame element with respect to the media field, a visual orientation results for the user in order to bring the movement and/or movement change felt by him by use of his sense of equilibrium into harmony with the displayed perspective, which is an important requirement for avoiding motion sickness. The described method thus uses cognitive processing of the perspective displayed by use of the image data or image stream, in order to obtain an influence in the user on his reaction to acceleration forces to reduce the motion sickness.

The disclosure also includes embodiments, due to which additional advantages result.

In one embodiment, during the display of the velocity component (from the travel dynamics data of the motor vehicle), the movement of the artificial environment is shown faster by an amplification factor greater than 1 than the movement of the real environment. The amplification factor can be in a range of 2 to 20. If the amplification factor is 10, for example, at a travel velocity of 10 km/h of the motor vehicle in the real environment, a corresponding relative movement of the artificial environment with respect to the frame element which corresponds to 100 km/h results. The amplification factor can also be set as a function of which absolute value the travel velocity of the motor vehicle has. An amplification factor greater than 1 amplifies the visual perception of a velocity change (i.e., an acceleration or deceleration of the motor vehicle), so that a further visual representation of the perceived acceleration force is provided here, which can further reduce the motion sickness.

In one embodiment, the media field has an extension angle in the horizontal and/or vertical direction less than 35% in the displayed perspective. The extension angle is measured here on the viewing angle or vision angle. The extension is for example in a range less than 30% or equal to 30% for the horizontal and vertical directions. The extension angle thus for example shows the media field in the region of the so-called foveal vision of the user. The extension angle in the horizontal and/or horizontal direction is for example greater than 15° here, however, for example the extension angle in the horizontal and/or horizontal direction may be greater than 20° or equal to 20°. The user can thus focus on the media field and can thus perceive the media content in a focused manner, while he perceives movement by use of the extra-foveal vision or the peripheral vision, namely the movement of the frame element and the artificial environment, which visually conveys the movement of the motor vehicle in the real environment to him. Since the eye is more sensitive for movement perception in the peripheral region than in the foveal region, the advantage results due to the extension angle (reduced to the foveal vision) of the media field that a particularly large region of the field of view of the user is made use of to visually convey the velocity component and the acceleration component of the vehicle dynamics data, since the movement of the artificial environment and the inclination of the frame element is recognizable.

In one embodiment, the media content is displayed in a partially transparent manner having an opacity of greater than 70% and less than 100% in the media field. In this way, one can thus partially see through the media field, wherein the transparency is correspondingly in a range greater than 0% and less than 30% inversely to the opacity. One sees the artificial environment overlaid through the media field. The movement of the artificial environment is thus also displayed in the media field. This advantageously assists in the reduction of the motion sickness.

In one embodiment, a longitudinal acceleration of the motor vehicle specified in the acceleration component (velocity increase or velocity reduction) is shown as a longitudinally-tilting frame element. The frame element thus tilts forward during a braking maneuver (i.e., it inclines downward or shifts downward with respect to the media field), and tilting to the rear is displayed during a velocity reduction (i.e., the frame element inclines upward or shifts upward with respect to the media field). The reaction or change of the frame element thus corresponds with the experience of the user that a motor vehicle executes a pitching movement when a longitudinal acceleration occurs. Due to this correspondence with experience, the visual representation of the acceleration component can be presented to the user consistently with his expected visual impression.

In one embodiment, a lateral acceleration of the motor vehicle indicated in the acceleration component is shown as a lateral tilt or rotation of the frame element with respect to the media field, wherein right cornering is displayed as tilting or rotating of the frame element to the right (i.e., a rotation clockwise) and left cornering is displayed as tilting or rotating of the frame element to the right (i.e., a rotation counterclockwise). This corresponds to a rolling behavior or tilting behavior of an aircraft. It has resulted that visually conveying a lateral acceleration of the motor vehicle in this way is perceived by the user as particularly advantageous in the reduction of the motion sickness.

In one embodiment, the frame element has the partially transparent region. The frame element can be displayed completely as a partially transparent element or only a partial region of the frame element can be displayed as partially transparent. An opacity of the frame element in the partially transparent region is at most 50% here. In other words, the frame element is shown at least 50% or more than 50% transparent. A partially transparent display can be effectuated by use of so-called alpha blending. The artificial environment is displayed or made visible through the partially transparent region of the frame element. In this way, the frame element is prevented from adjusting or blocking the view to the user of the artificial environment and/or movement components or movement impressions which are conveyed by the artificial environment.

In one embodiment, the media field is displayed independently of the acceleration component. The media field is for example also displayed independently of the velocity component. The media field offers as a visual anchor point or image content anchored with an artificial horizon. The advantage results in this way that the user maintains the orientation in space even if, for example, cornering occurs.

In one embodiment, exclusively the frame element is tilted in the described way by use of the acceleration component. Of course, the acceleration component also acts indirectly on the movement velocity of the artificial environment, since this changes with time. The acceleration component itself, i.e., its absolute current value, is for example exclusively visually conveyed or displayed by use of the frame element, however. In other words, for example the artificial environment remains non-tilted or non-inclined when an acceleration force or acceleration component acts. The advantage results in this way that the user preserves his spatial orientation.

In order to carry out the method described herein in a motor vehicle, a control device for data glasses of a motor vehicle is provided. The control device includes a processor unit, which is configured to carry out one or more embodiments of the method described herein. The processor unit can include for this purpose at least one microprocessor and/or at least one microcontroller. The processor unit can include program code which can include program instructions which are configured, upon execution by the processor unit, to execute the one or more embodiments of the method described herein. The program code can be stored in a data memory of the processor unit.

Finally, also described herein is a motor vehicle having data glasses and an embodiment of the control device described herein. The motor vehicle described herein is for example designed as an automobile, for example as a passenger vehicle or truck.

The disclosure also includes the combinations of the features of the described embodiments.

BRIEF DESCRIPTION OF THE DRAWINGS

These and other aspects and advantages will become more apparent and more readily appreciated from the following description of the example embodiments, taken in conjunction with the accompanying drawings, in which:

FIG. 2 is a schematic illustration of a perspective as can be displayed in data glasses in the motor vehicle of FIG. 1 by a control device.

DETAILED DESCRIPTION

Figure 1:
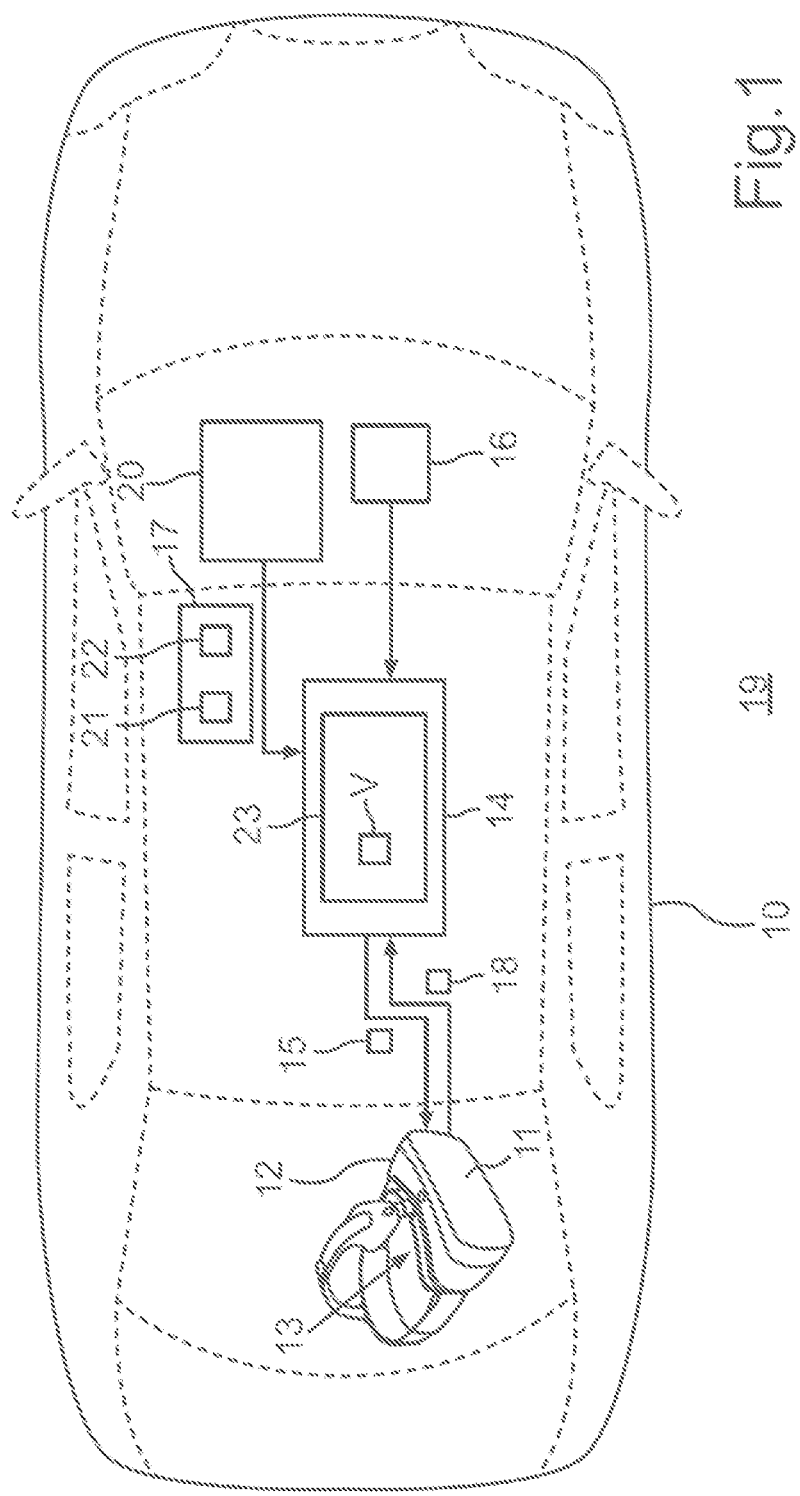
FIG. 1 is a schematic illustration of an embodiment of the motor vehicle described herein.

The example embodiments explained hereinafter are examples. In the example embodiments, the described components of the embodiments each represent individual features to be considered independently of one another, which each also refine the disclosure independently of one another. Therefore, the disclosure is also to include combinations of the features of the embodiments other than those shown. Furthermore, the described embodiments can also be supplemented by further features already described.

In the drawings, identical reference characters each identify functionally-identical elements.

FIG. 1 shows a motor vehicle 10, which can be an automobile, for example a passenger vehicle or truck. The motor vehicle 10 can be provided for use, for example by a passenger or (in the case of an autonomous driving mode) by a driver. The data glasses 11 can have the eye part 12, which closes off the eyes of the user in a vision-tight manner when the data glasses are worn. A display unit 13 can be integrated into the eye part 12, by use of which graphic display content can be displayed to the user in his field of view when wearing the data glasses 11. A control device 14 can generate graphic data 15 for this purpose to control the data glasses 11 and to define the display content on the display unit 13. The control device 14 can thus for example display media content 16 by use of the data glasses 11, which can be, for example, a video film and/or photographs and/or image contents from the Internet and/or a text, for example an email or an SMS (short message service), and/or a presentation. While the motor vehicle 10 is driving, however, the hazard exists that the user will feel sick, i.e. that he suffers from motion sickness, because his vision cannot register the environment of the user through the eye part 12, so that the user does feel acceleration forces with his sense of equilibrium, but also has to see a visually corresponding event thereto, so that motion sickness is reduced or prevented.

For this purpose, it is provided in the motor vehicle 10 that the control device uses vehicle dynamics data 17 and glasses dynamics data 18. The glasses dynamics data 18 describe a movement of the data glasses 11 with respect to the motor vehicle and/or an environment 19 of the motor vehicle. The glasses dynamics data 18 can be generated, for example, by use of at least one acceleration sensor which can be integrated into the data glasses 11, and/or by use of radio sensors and/or optical sensors, which can be provided in the motor vehicle 10 and register a relative movement of the data glasses 11.

The vehicle dynamics data 17 can be received in a way known per se from a sensor unit 20 of the motor vehicle 10, for example via a communication bus, for example a CAN bus (CAN—Controller Area Network). The vehicle dynamics data can for example describe a movement component 21 and an acceleration component 22. The movement component 21 can specify, for example a travel direction and/or a travel velocity. The acceleration component 22 can describe, for example, a velocity change in the longitudinal direction and/or transverse direction and/or around a vertical rotational axis (yaw rate) and/or a pitch rate (rotation around a transverse axis) and/or roll rate (rotation around a longitudinal axis).

The movement component can describe a yaw movement, i.e. a rotation around a vertical rotational axis, a pitch movement around a transverse axis, and/or a roll movement around a longitudinal axis of the motor vehicle 10.

The control device 14 can be implemented, for example, on the basis of at least one control unit and can include a processor unit 23 for carrying out the following method.

The control device 14 can, for example, by use of the graphic data 15, display the media content 16 to the user by use of the data glasses 11 in the way shown in FIG. 2, in order to avoid or reduce the user feeling motion sickness when viewing the media content 16.

FIG. 2 illustrates a perspective 24 as can be conveyed to the user as a view into a virtual space 25 by use of the display unit 13. A shift 26 of the view or a viewing direction change which shows the displayed image detail or the displayed view into the virtual space 25 can be set as a function of the glasses dynamics data 18. The shift 26 corresponds to a camera pivot.

In the perspective 24, the media content 16 can be displayed in a media field 27, which can be represented, for example as a rectangle or an artificial projection surface. A horizontal extension angle 28 and/or a vertical extension angle 29 can fill up the field of view of the user up to an extension angle of 35°, but may be less. The media content 16 can for example be displayed in the media field 27 by use of a partial transparency 30, through which an artificial environment 31 is also visible in the media field 27, which can be further displayed outside the media field 27. A relative movement 32 of the artificial environment 31 with respect to the virtual viewpoint of the user, i.e., with respect to the perspective 24, can be adapted on the basis of the movement component 21 of the vehicle dynamics data 17 to a travel velocity of the motor vehicle 10 through the environment 19. An amplification factor V greater than 1 relating to the movement 32 of the artificial environment in relation to the travel velocity can be provided here. Furthermore, a frame element 33 can be displayed in the perspective 24, which can entirely or partially enclose the media field 27. A frame of a window of a cockpit can be displayed by use of the frame element 33, for example. A partial transparency can also be provided for the frame element 33 at least for a region 33'.

The frame element 33 can carry out an inclination movement or inclination 34 with respect to the media field 27, wherein tilting 35, i.e., a shift upward or downward with respect to the media field 27, can be set as a function of the acceleration component 22 of the vehicle dynamics data if it is a longitudinal acceleration. In the case of a lateral acceleration, an inclination or a tilt of the frame element 33 with respect to the media field 27 and the artificial environment 31 can be provided.

Overall, a combination of multiple approaches therefore results, which have led to a reduction of motion sickness in test subjects. The size of the media field or movie screen can for example only be at most 20° to 30° horizontally (the angle relates to an angle spanned by the eye, which represents a percentage of the field of view).

The media field 27 may be displayed slightly transparent (10% to 20% transparency as a guideline).

In addition to the media field 27, a cockpit or generally a frame element may be displayed, in which the user is located. The frame element for example has the following properties, for example as a cockpit.

For example, the frame element may have the property that longitudinal accelerations of the motor vehicle result in tilting of the cockpit forward and backward, where a braking maneuver represents tilting forward here.

For example, the frame element may have the property that lateral accelerations result in tilting to the left and right, wherein right-hand curves, i.e., an acceleration to the left, result in tilting of the frame element to the right (similarly to the flight dynamics of an aircraft).

For example, the frame element may have the property that the frame element or cockpit has a transparency of at least 50% (alpha value for the alpha blending) in a partially transparent region 33', for example in the entire region. Objects 36 passing by may be perceptible through this without vision restriction.

For example, the frame element may have the property that the media field 27 has to be decoupled from the tilting of the frame element 33 (for example shown as a cockpit).

For example, the frame element may have the property that the movement of the camera or the shift 26 of the perspective has to be decoupled from the tilting of the frame element 33 (for example shown as a cockpit).

The specified values are for example guidelines and can be set or defined by a person skilled in the art in the exact implementation.

The motion sickness when consuming media content (for example, classic media, for example films, series, texts, and/or presentations) may be reduced by the described measures.

A description has been provided with reference to various examples, but it will be understood that variations and modifications can be effected within the spirit and scope of the claims which may include the phrase "at least one of A, B and C" as an alternative expression that means one or more of A, B and C may be used, contrary to the holding in *Superguide v. DIRECTV*, 358 F3d 870, 69 USPQ2d 1865 (Fed. Cir. 2004).

The invention claimed is:

1. A method of reducing motion sickness of a user when viewing a media content using data glasses during a journey in a motor vehicle, the method comprising:
   registering vehicle dynamics data, which describe a movement of the motor vehicle with respect to a real environment of the motor vehicle, and glasses dynamics data, which describe a movement of the data glasses with respect to the motor vehicle and/or the real environment; and
   controlling, by a controller, displaying of a perspective forming a virtual viewpoint for the user using the data glasses, based on the vehicle dynamics data and the glasses dynamics data by,
      displaying a frame element in the perspective, displaying the media content in a media field visible through the frame element, and displaying an artificial environment adjacent to the frame element and/or through a partially transparent region of the frame element, so that the frame element at least partially encloses the media field in the perspective with the artificial environment displayed adjacent to the frame element and/or through the partially transparent region of the frame element,
      representing a velocity of the motor vehicle in the perspective, based on a velocity component of the vehicle dynamics data, by displaying a movement of the artificial environment with respect to the frame element, representing an acceleration of the motor vehicle in the perspective, based on an acceleration component of the vehicle dynamics data, by displaying an inclination of the frame element with respect to the media field, and representing a movement of the data glasses in the perspective, based on a movement component of the glasses dynamics data, by shifting the perspective or shifting the perspective without the media field.

2. The method according to claim 1, wherein the movement of the artificial environment is displayed faster than a movement of the real environment by an amplification factor greater than one.

3. The method according to claim 1, wherein the displayed frame element forming the perspective by at least partially enclosing the media field, is displayed to have an extension angle less than 35° in a horizontal direction and/or in a vertical direction.

4. The method according to claim 1, wherein
the media content is displayed in a partially transparent manner such that the media content has an opacity of greater than 70% and less than 100%; and
the artificial environment is superimposed in the media field.

5. The method according to claim 1, wherein
the representing the acceleration component with the inclination of the frame element includes,
displaying a longitudinal acceleration of the motor vehicle specified in the acceleration component as a longitudinal tilt of the displayed frame element,
displaying a braking maneuver as a tilt forward, and
displaying a velocity increase as a tilt to rear.

6. The method according to claim 1, wherein
the representing the acceleration component with the inclination of the frame element includes,
displaying a lateral acceleration of the motor vehicle specified in the acceleration component as a rotation of the displayed frame element,
displaying right cornering as a rotation of the displayed frame element to the right, and
displaying left cornering as a rotation of the displayed frame element to the left.

7. The method according to claim 1, wherein
the displayed frame element includes a partially transparent region, and
an opacity of the displayed frame element in the partially transparent region is at most 50%.

8. The method according to claim 1, wherein displaying the media field includes displaying the media field independently of the acceleration component.

9. The method according to claim 1, wherein the representing the acceleration component with the inclination of the frame element includes exclusively tilting the displayed frame element based on the acceleration component.

10. A controller for data glasses of a motor vehicle, the controller comprising:
a memory configured to store instructions; and
a processor configured to execute the instructions stored in the memory to:
receive vehicle dynamics data, which describe a movement of the motor vehicle with respect to a real environment of the motor vehicle, and glasses dynamics data, which describe a movement of the data glasses with respect to the motor vehicle and/or the real environment; and control displaying of a perspective forming a virtual view point for a user using the data glasses, based on the vehicle dynamics data and the glasses dynamics data by,
displaying a frame element in the perspective, displaying a media content in a media field visible through the frame element, and displaying an artificial environment adjacent to the frame element and/or through a partially transparent region of the frame element, so that the frame element at least partially encloses the media field in the perspective with the artificial environment displayed adjacent to the frame element and/or through the partially transparent region of the frame element,
representing a velocity of the motor vehicle in the perspective, based on a velocity component of the vehicle dynamics data, by displaying a movement of the artificial environment with respect to the frame element,
representing an acceleration of the motor vehicle in the perspective, based on an acceleration component of the vehicle dynamics data, by displaying an inclination of the frame element with respect to the media field, and
representing a movement of the data glasses in the perspective, based on a movement component of the glasses dynamics data, by shifting the perspective or shifting the perspective without the media field.

11. The controller according to claim 10, wherein the movement of the artificial environment is displayed faster than a movement of the real environment by an amplification factor greater than one.

12. The controller according to claim 10, wherein the displayed frame element forming the perspective by at least partially enclosing the media field, is displayed to have an extension angle less than 35° in a horizontal direction and/or in a vertical direction.

13. The controller according to claim 10, wherein
the media content is displayed in a partially transparent manner such that the media content has an opacity of greater than 70% and less than 100%; and
the artificial environment is superimposed in the media field.

14. The controller according to claim 10, wherein
the representing the acceleration component with the inclination of the frame element includes,
displaying a longitudinal acceleration of the motor vehicle specified in the acceleration component as a longitudinal tilt of the displayed frame element,
displaying a braking maneuver as a tilt forward, and
displaying a velocity increase as a tilt to rear.

15. The controller according to claim 10, wherein
the representing the acceleration component with the inclination of the frame element includes
displaying a lateral acceleration of the motor vehicle specified in the acceleration component as a rotation of the displayed frame element,
displaying right cornering as a rotation of the displayed frame element to the right, and
displaying left cornering as a rotation of the displayed frame element to the left.

16. The controller according to claim 10, wherein
the displayed frame element includes a partially transparent region, and an opacity of the displayed frame element in the partially transparent region is at most 50%.

17. The controller according to claim 10, wherein the media field is displayed independently of the acceleration component.

18. The controller according to claim 10, wherein the representing the acceleration component with the inclination of the frame element includes exclusively tilting the displayed frame element based on the acceleration component.

* * * * *